(12) United States Patent
Ogle

(10) Patent No.: US 9,314,591 B2
(45) Date of Patent: Apr. 19, 2016

(54) CATHETER SHAPE ADJUSTMENT MECHANISM

(75) Inventor: David Ogle, Cowan (AU)

(73) Assignee: CATHRX LTD, Homebush Bay (AU)

( * ) Notice: Subject to any disclaimer, the term of this patent is extended or adjusted under 35 U.S.C. 154(b) by 213 days.

(21) Appl. No.: 13/697,323

(22) PCT Filed: May 10, 2011

(86) PCT No.: PCT/AU2011/000532
§ 371 (c)(1),
(2), (4) Date: Nov. 9, 2012

(87) PCT Pub. No.: WO2011/140586
PCT Pub. Date: Nov. 17, 2011

(65) Prior Publication Data
US 2013/0060237 A1 Mar. 7, 2013

Related U.S. Application Data

(60) Provisional application No. 61/333,574, filed on May 11, 2010.

(51) Int. Cl.
*A61M 31/00* (2006.01)
*A61M 25/01* (2006.01)

(52) U.S. Cl.
CPC ............ *A61M 25/01* (2013.01); *A61M 25/0102* (2013.01); *A61M 25/0133* (2013.01); *A61M 25/0136* (2013.01); *A61M 25/0147* (2013.01); *A61M 25/0152* (2013.01); *A61M 2025/0161* (2013.01)

(58) Field of Classification Search
CPC ............ A61M 25/01; A61M 25/0102; A61M 25/0105; A61M 25/0133; A61M 25/0136; A61M 25/0147; A61M 25/0152; A61M 2025/0161; A61M 2025/0163
USPC .......... 604/95.01, 95.04–95.05, 264; 606/129
See application file for complete search history.

(56) References Cited

U.S. PATENT DOCUMENTS

| 5,327,905 A | 7/1994 | Avitall |
| 5,383,923 A | 1/1995 | Webster |
| 5,545,200 A * | 8/1996 | West et al. ..................... 607/122 |

(Continued)

FOREIGN PATENT DOCUMENTS

| CA | 2138236 A1 | 5/1996 |
| EP | 904797 A2 | 3/1999 |

(Continued)

OTHER PUBLICATIONS

PCT International Search Report, International Application No. PCT/AU2011000532, mailed Sep. 8, 2011, four (4) pages.

(Continued)

*Primary Examiner* — Quynh-Nhu H Vu
(74) *Attorney, Agent, or Firm* — TraskBritt

(57) ABSTRACT

A catheter includes a handle, a catheter sheath and a stylet having a shaped distal part received within the catheter sheath. The catheter further has a shape adjustment mechanism including a stylet carrier displaceably carried by the handle and a shape adjuster in the form of a collar rotatable about the handle. Rotational movement of the shape adjuster imparts a motion to the stylet carrier to adjust the shape of the distal part of the stylet.

19 Claims, 11 Drawing Sheets

(56) References Cited

U.S. PATENT DOCUMENTS

| | | | |
|---|---|---|---|
| 5,611,777 A * | 3/1997 | Bowden et al. | 604/95.01 |
| 5,656,030 A | 8/1997 | Hunjan et al. | |
| 5,662,606 A | 9/1997 | Cimino et al. | |
| 5,666,970 A | 9/1997 | Smith | |
| 5,779,669 A | 7/1998 | Haissaguerre et al. | |
| 5,792,104 A | 8/1998 | Speckman et al. | |
| 5,910,129 A | 6/1999 | Koblish et al. | |
| 5,987,344 A | 11/1999 | West et al. | |
| 6,013,052 A | 1/2000 | Durman et al. | |
| 6,263,224 B1 * | 7/2001 | West | 600/373 |
| 6,542,781 B1 | 4/2003 | Koblish et al. | |
| 6,554,794 B1 * | 4/2003 | Mueller et al. | 604/95.04 |
| 6,805,675 B1 | 10/2004 | Gardeski et al. | |
| 2002/0072712 A1 | 6/2002 | Nool et al. | |
| 2002/0165484 A1 | 11/2002 | Bowe et al. | |
| 2003/0171723 A1 | 9/2003 | Ponzi | |
| 2006/0264819 A1 | 11/2006 | Fischer et al. | |
| 2007/0225641 A1 | 9/2007 | Schneider et al. | |
| 2009/0024084 A1 | 1/2009 | Khosla et al. | |
| 2009/0299282 A1 | 12/2009 | Lau et al. | |
| 2013/0053876 A1 * | 2/2013 | Ogle | 606/170 |
| 2013/0060236 A1 * | 3/2013 | Ogle | 604/528 |
| 2013/0060237 A1 | 3/2013 | Ogle | |

FOREIGN PATENT DOCUMENTS

| | | |
|---|---|---|
| EP | 1676595 A1 | 7/2006 |
| EP | 1323448 A2 | 9/2008 |
| EP | 2116272 A1 | 11/2009 |
| WO | 9637252 | 11/1996 |
| WO | WO9634653 A1 | 11/1996 |
| WO | WO2006092014 A1 | 9/2006 |
| WO | WO2006135988 A1 | 12/2006 |
| WO | WO2007038539 A1 | 4/2007 |
| WO | 2007089676 A1 | 8/2007 |
| WO | 2007128065 A1 | 11/2007 |
| WO | 2009114908 A1 | 9/2009 |
| WO | WO2009142120 A1 | 11/2009 |

OTHER PUBLICATIONS

Written Opinion of the International Search Authority for International Application No. PCT/AU2011/000532, dated Sep. 7, 2011, 9 pages.

International Preliminary Report on Patentability, for International Application No. PCT/AU2011/000532, dated Nov. 13, 2012, 10 pages.

European Supplemental Search Report for European Application No. EP1779964, dated Dec. 20, 2013, 8 pages.

* cited by examiner

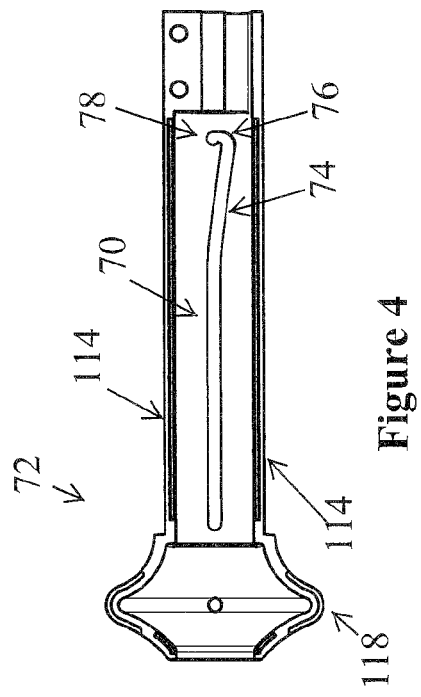
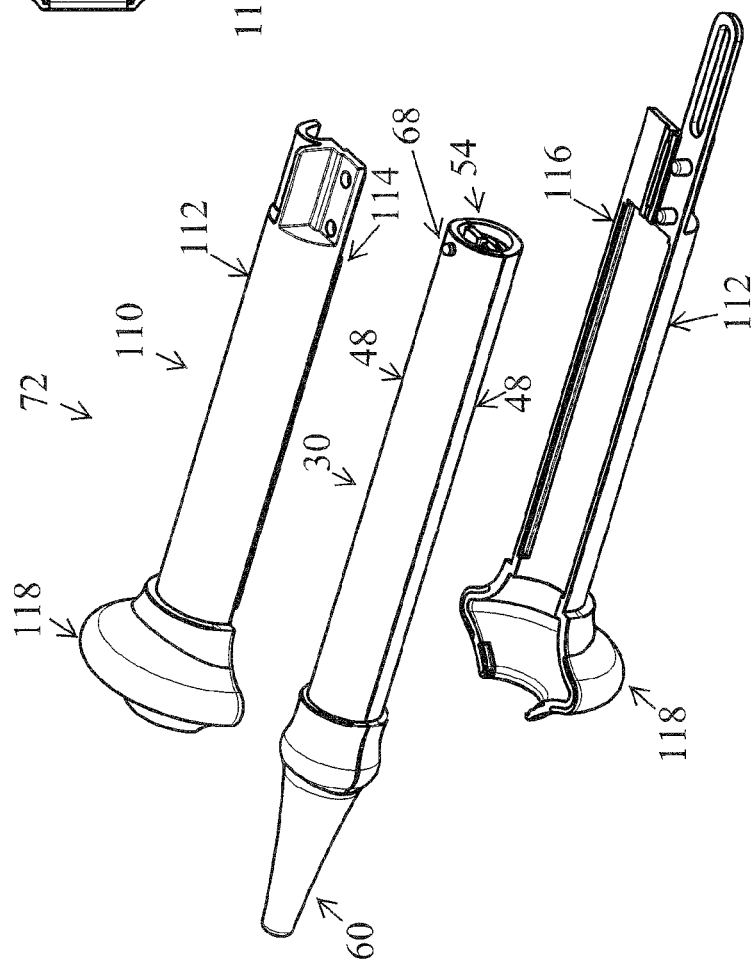
Figure 4
Figure 5

CATHETER SHAPE ADJUSTMENT MECHANISM

CROSS-REFERENCE TO RELATED APPLICATIONS

This application is a national phase entry under 35 U.S.C. §371 of International Patent Application PCT/AU2011/000532, filed May 10, 2011, designating the United States of America and published in English as International Patent Publication WO 2011/140586 A1 on Nov. 17, 2011, which claims the benefit under Article 8 of the Patent Cooperation Treaty and under 35 U.S.C. §119(e) to U.S. Provisional Patent Application Ser. No. 61/333,574, filed May 11, 2010, the disclosure of each of which is hereby incorporated herein by this reference in its entirety.

TECHNICAL FIELD

This disclosure relates, generally, to a catheter and, more particularly, to a catheter shape adjustment mechanism and to a catheter including the shape adjustment mechanism.

BACKGROUND

Any discussion of the prior art throughout the specification should in no way be considered as an admission that such prior art is widely known or forms part of common general knowledge in the field.

Catheters are commonly used in medical practice to examine and treat the heart. They may be inserted into the cardiovascular system of the patient through small punctures in the skin, usually in the neck or groin area. Typically, a catheter includes a catheter sheath carrying several electrodes at the tip of the sheath and a control handle for deflecting the tip of the catheter to steer or guide the catheter. The electrodes attached to the catheter sheath can be used to sense electrical signals to identify particular heart conditions or to treat these conditions.

Some catheters carry a multi-electrode loop or lasso structure at the tip of the catheter sheath. One of the advantages of the multi-electrode loop is that sensing can be achieved over a larger area. For example, electrical signals can be sensed around an entire pulmonary vein. Because each biological site is unique in teams of dimensions and geometry, a physician may have to use multiple catheters having different characteristics during a procedure. Multiple different catheters varying in size or shape may be used in order to access the desired part of the anatomy. Using multiple catheters and sequentially removing and inserting them can be difficult and time-consuming. It is also possible that the loop structure snags on tissue while the physician uses the catheter during a medical procedure.

DISCLOSURE

It is an object of the present invention to overcome or ameliorate at least one of the disadvantages of the prior art, or to provide a useful alternative.

According to an embodiment of the invention, there is provided a catheter shape adjustment mechanism that includes a catheter handle comprising an elongate handle body having a proximal end and a distal end, with a passage extending between the proximal end and the distal end, a stylet carrier displaceably mounted in the passage of the handle body, at least a component of a multi-component stylet being mountable to the stylet carrier, a shape adjuster rotatably carried on an exterior of the handle body, the shape adjuster being rotatable about a longitudinal axis of the handle body, and complementary guide formations carried by the stylet carrier and the shape adjuster so that rotary motion applied to the shape adjuster imparts a predefined motion to the stylet carrier to adjust the shape of a distal part of the stylet during use.

The stylet carrier may be in the form of a slide that is axially slidable in the handle body.

In addition, the stylet carrier may include a mounting formation for mounting a component of the stylet, the stylet being a multi-component stylet, as defined. The complementary guide formations may comprise a camming groove defined on an operatively inner surface of the shape adjuster and a follower carried by the stylet carrier, the follower protruding through a slot defined in the handle body to be received in the camming groove of the shape adjuster.

In an embodiment, the catheter handle may comprise a plurality of shell members that are assembled to form the handle body and that can be at least partially separated from each other to access an interior of the handle body. The handle body may also define a receiving formation for rotatably receiving the shape adjuster. The receiving formation may be defined by a waisted region of the handle body.

In an embodiment, the shape adjuster is in the form of a collar received in the receiving formation of the handle body. The collar may further comprise a plurality of separable parts to enable the collar to be fit into position about the handle body.

According to another embodiment, there is provided a method of fabricating a shape adjustment mechanism as described above.

An embodiment of the invention provides a catheter that includes a catheter handle comprising an elongate handle body having a proximal end and a distal end and a passage extending between the proximal end and the distal end, and a shape adjustment mechanism carried by the handle body, the shape adjustment mechanism comprising a stylet carrier displaceably mounted in the passage of the handle body and a shape adjuster rotatably carried on an exterior of the handle body, the shape adjuster being rotatable about a longitudinal axis of the handle body, the stylet carrier and the shape adjuster having complementary guide formations so that rotary motion applied to the shape adjuster imparts a predefined motion to the stylet carrier. The catheter further comprises a multi-component stylet carried by the catheter handle with a distal part of the stylet being formed into a predetermined shape, the stylet comprising at least a first component connected to the stylet carrier and a second component arranged in the handle body so that relative movement between the stylet carrier, under the action of the shape adjuster, and the handle body results in a change of shape of the distal part of the stylet.

The catheter may include a steering control mechanism displaceably carried by the handle body, the steering control mechanism effecting steering of the stylet. The stylet may comprise three components, the first component being mounted to the stylet carrier, one of the second component and a third component being mounted to the steering control mechanism and the other of the second component and the third component being fast with the handle body.

An embodiment of the invention provides that the catheter includes a catheter sheath mounted to a distal end of the catheter handle, the catheter sheath defining a lumen in which the stylet is received so that the preformed shape at the distal part of the stylet is imparted to a distal part of the catheter sheath. The catheter sheath may be carried on a shape release mechanism, the shape release mechanism being displaceably carried by the handle body.

BRIEF DESCRIPTION OF THE DRAWINGS

Preferred embodiments of the invention will now be described, by way of example only, with reference to the accompanying drawings in which:

FIG. 4 shows a cross-sectional bottom view of a part of a steering control mechanism of the catheter handle carrying a component of the shape release mechanism;

FIG. 5 shows a three-dimensional, exploded view of the steering control mechanism and shape release mechanism of the catheter;

DETAILED DESCRIPTION

Figure 1:
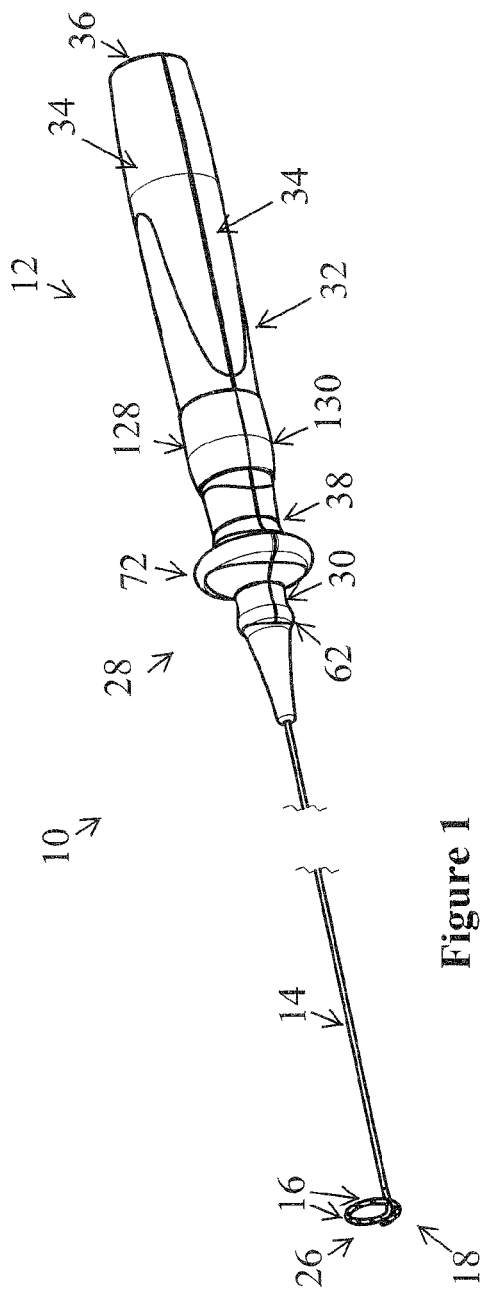
FIG. 1 shows a three-dimensional view of a catheter with a shape release mechanism in an inoperative position.

In the drawings, reference numeral 10 generally designates an embodiment of a catheter. The catheter 10 comprises a catheter handle 12 from which a catheter sheath or electrode sheath 14 projects. The catheter sheath 14 carries a plurality of electrodes 16 at a distal part 18 of the catheter sheath 14. The electrodes 16 are used for diagnostic and/or therapeutic purposes.

The catheter further includes a stylet 20 (shown in FIGS. 9 and 11-13). A proximal part 22 of the stylet 20 is received within the catheter handle 12, as will be described in greater detail below. The catheter sheath 14 has a lumen (not shown) in which the stylet 20 is received. As shown more clearly in FIG. 12, a distal part 24 of the stylet 20 is pre-formed into a shape, more particularly a loop shape 26. However, it will be appreciated that the distal part 24 of the stylet 20 could be pre-formed into any other non-rectilinear shape such as, for example, a helix, a tapering helix, a pig tail shape, or any other desired shape.

The stylet 20 fits within the lumen of the catheter sheath 14 and the loop shape 26 of the distal part 24 of the stylet 20 is imparted to the distal part 18 of the catheter sheath 14 as shown in FIG. 1. For ease of explanation, the disclosure will be described with reference to the shape at the distal part 24 of the stylet 20 being the loop shape 26. However, it will be appreciated that what follows could be applicable to any other stylet 20 having a shaped distal part 24.

Figure 2:
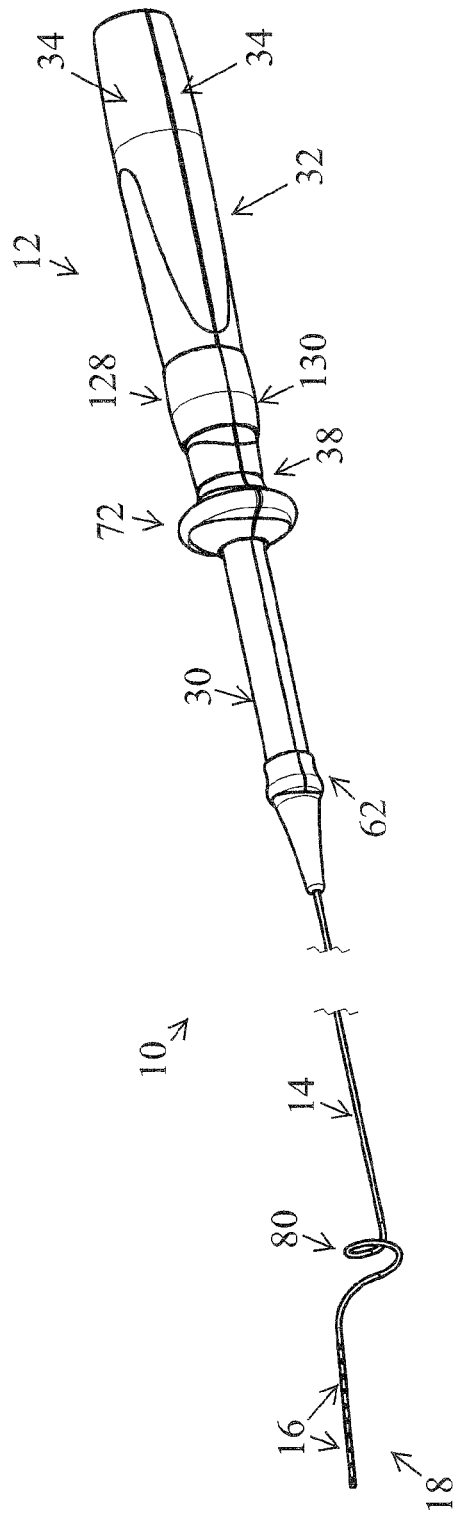
FIG. 2 shows a three-dimensional view of the catheter with the shape release mechanism in an operative position.

In an embodiment, the catheter 10 includes a shape release mechanism 28. The shape release mechanism 28 comprises the catheter handle 12 and an elongate catheter sheath carrier in the form of a sleeve 30, which is slidably received in the handle 12 to protrude distally from the handle 12. The shape release mechanism 28 enables releasing the shape that the stylet 20 imparts on the distal part 18 of the catheter sheath 14. This is achieved by pushing the catheter sheath 14 forward so that the distal part 24 of the stylet 20 relocates to a position proximal to the distal part 18 of the electrode sheath as shown at 80 in FIG. 2. In this operative position, the distal part 24 of the stylet 20 and the distal part 18 of the catheter sheath 14 are no longer in register with one another. FIG. 2 shows the catheter shape release mechanism 28 in its operative position when the catheter sheath 14 has been pushed forward and the distal parts 18, 24, respectively, of the catheter sheath 14 and the stylet 20 are no longer in register with one another.

The handle 12 comprises a handle body 32. The handle body 32 is made up of a plurality of shell parts 34, shown most clearly in FIG. 8. In the illustrated embodiment, the handle body 32 comprises two shell parts that are substantially mirror images of each other. The handle body 32 has a proximal end 36 and a distal end 38. A passage 40 (FIG. 8) extends between the proximal end 36 and the distal end 38 of the handle body 32.

Figure 8:
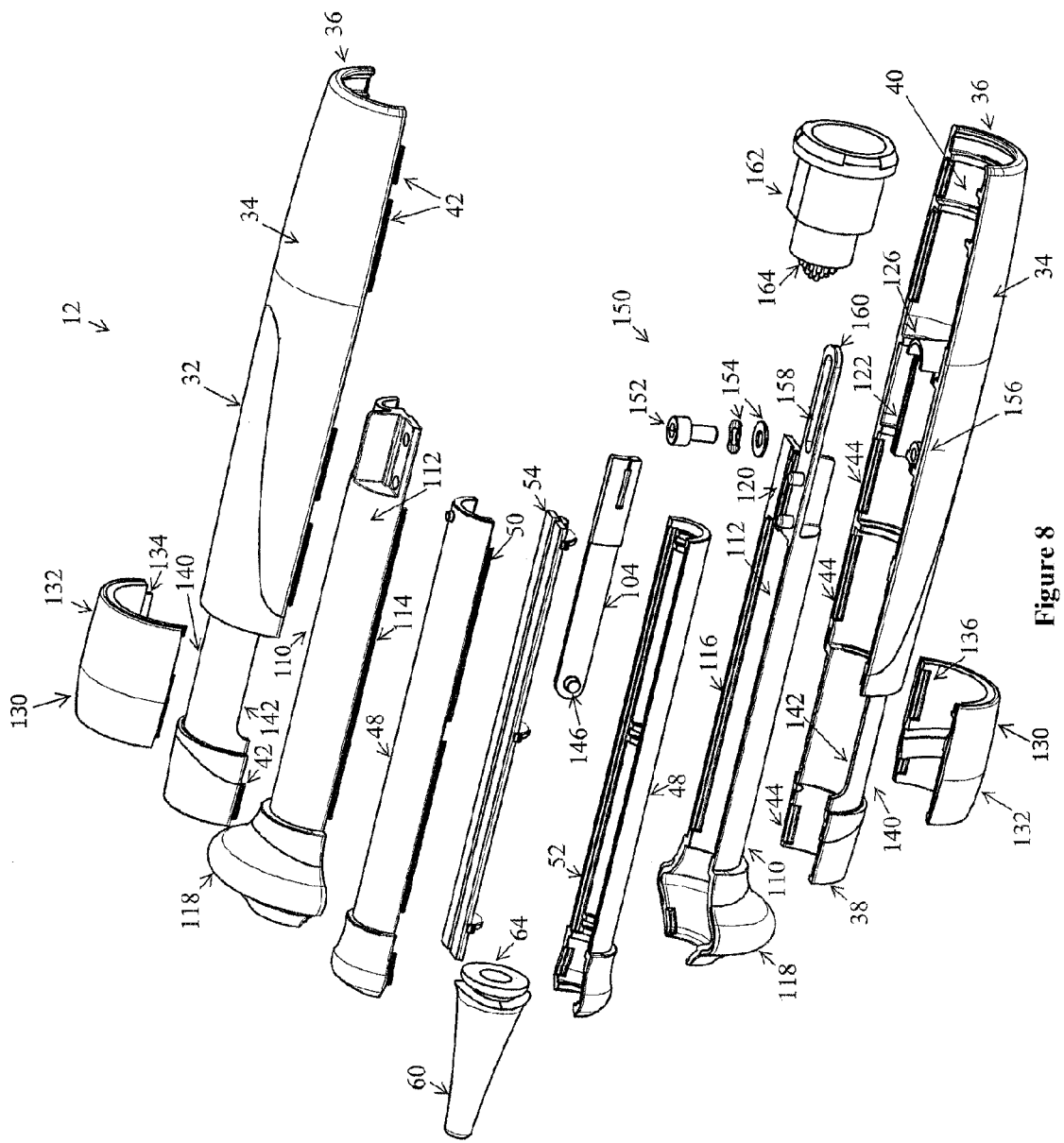
FIG. 8 shows a three-dimensional, exploded view of a handle of the catheter.

In the embodiment illustrated in FIG. 8, the two shell parts 34 are secured together by clips 42, carried on one of the shell parts 34, which are received in complementary receiving formations 44 in the other shell parts 34.

Figure 14:
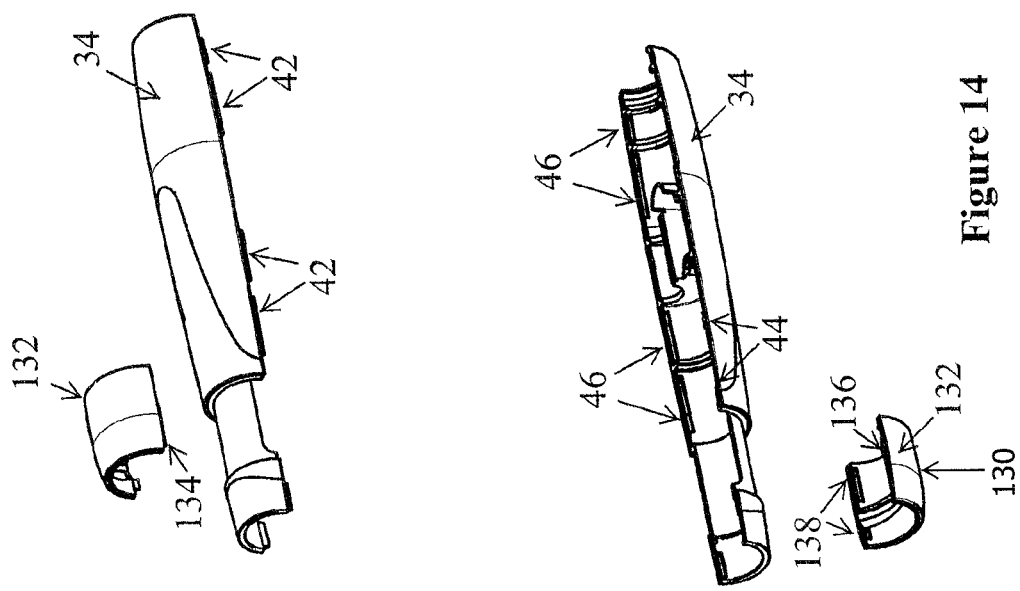
FIG. 14 shows a three-dimensional, exploded view of another embodiment of the handle of the catheter.

In the embodiment shown in FIG. 14, only one side of each shell part 34 has the clips 42 or receiving formations 44, as the case may be. The other side of the shell parts 34 of the handle body 32 are hinged together with wings 46 of the hinges shown in FIG. 14.

Regardless of the manner in which the shell parts 34 connect together, it is a simple process to open the handle body 32 by disengaging the shell parts 34 to enable access to be gained to an interior of the handle body 32. Further, it will be appreciated that, instead of clips, the shell parts 34 could be held together in other ways, for example, by being screwed together, by means of one or more spring clips received about the handle body 32, or the like.

Figure 3:
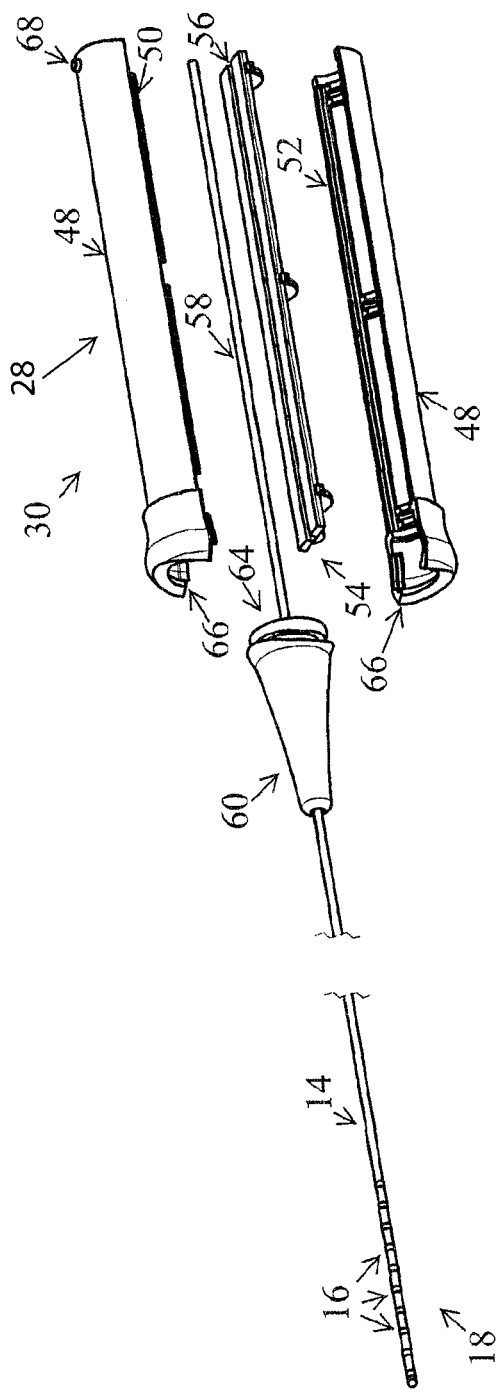
FIG. 3 shows a three-dimensional, exploded view of the catheter sheath carrier of the catheter shape release mechanism together with the catheter sheath.

With reference to FIG. 3, the sleeve 30 of the shape release mechanism 28 comprises two parts 48. In the illustrated embodiment, the two parts 48 clip together via clips 50 and locating formations 52. As described above with reference to the shell parts 34 of the handle body 32, it will be appreciated that these parts 48 could also be hinged together and clipped or screwed together to form the sleeve 30.

The sleeve 30 surrounds a support member 54 for supporting the catheter sheath 14. The support member 54 has a longitudinally extending channel 56 formed in it. A proximal part 58 of the catheter sheath 14 is supported in the channel 56 of the support member 54. If desired, the proximal part 58 can be bonded in the channel 56 by means of a suitable adhesive.

The shape release mechanism 28 also includes a strain relief 60. In the embodiment shown in the accompanying figures, the strain relief 60 is conically shaped to allow the catheter sheath 14 to move and bend without putting stress on the connection where the catheter sheath 14 meets the sleeve 30 of the shape release mechanism 28. The strain relief 60 is secured to a distal end 62 (FIGS. 1 and 2) of the sleeve 30. The strain relief 60 is of a resiliently flexible material and has a proximal collar 64, which engages a shoulder 66 on the parts 48 of the sleeve 30 to hold the strain relief 60 captive when the parts 48 of the sleeve 30 are secured together. The strain relief 60, being of a resiliently flexible material, also inhibits ingress of foreign matter, such as bodily fluid into the interior of the sleeve 30 and, therefore, the interior of the catheter handle 12 (FIGS. 1 and 2).

The shape release mechanism 28 includes complementary guide formations for guiding sliding displacement of the sleeve 30 relative to the handle body 32. The complementary guide formations comprise a pin 68 arranged at a proximal end of one of the parts 48 of the sleeve 30 (FIG. 5). A guide plate 70 (FIG. 4) is secured to a part of the catheter handle 12, more particularly, a steering control mechanism 72 of the catheter handle 12. The steering control mechanism 72 will be described in greater detail below.

The guide plate 70 defines a guide slot 74 that extends axially in the guide plate 70. The guide slot 74 is cranked and a locking arrangement in the form of a detent 76 is defined at a proximal end of the guide slot 74. Thus, when the sleeve 30 is in its retracted position as shown in FIG. 1, the pin 68 is received in the detent 76 at an extremity 78. To release the sleeve 30 to enable it to slide axially to the position as shown in FIG. 2, the sleeve 30 needs to be rotated so that the pin 68 moves away from the extremity 78 into alignment with the remainder of the guide slot 74. The sleeve 30 is then free to be extended to the position as shown in FIG. 2.

The purpose of the shape release mechanism 28 is to release the loop shape 26 when it snags on tissue in the patient's body during use. This can lead to complications and difficulty. As shown, the loop shape 26 is a tightly wound formation. However, by extending the catheter sheath 14 relative to the stylet 20 from the position shown in FIG. 1 to the position shown in FIG. 2, by extending the sleeve 30 relative to the handle 12, the distal part 24 of the stylet 20 is withdrawn from the distal part 18 of the catheter sheath 14 and adopts a position proximal the distal part 18 of the catheter sheath 14 as shown at 80 in FIG. 2. When the distal part 24 of the stylet 20 is withdrawn proximally relative to the distal part 18 of the catheter sheath 14, the tension in the distal part 24 of the stylet 20 is reduced, causing the distal part 24 to adopt a more drawn out, less tightly wound shape and facilitate disentanglement or release of the shaped part of the catheter sheath 14 from tissue in which it may have become entangled. In practice, if the loop structure of the catheter 10 snags on tissue, the user would unlock the locking arrangement, keeping the catheter sheath carrier sleeve 30 in place, and then pull back the catheter handle 12 and the stylet 20 while keeping the sleeve 30 in place. This way, the distal tip of the catheter sheath 14 stays in place where it snagged on tissue and once the loop of the stylet 20 is pulled back, the sheath becomes free again. It is also possible to reduce the size of the loop structure to assist in releasing the loop from the tissue by appropriate manipulation of a size-adjusting mechanism 128 described in more detail below.

As described above, the catheter handle 12 includes a steering control mechanism 72. This steering control mechanism 72 is used for steering the distal part 18 of the catheter sheath 14 through the patient's vasculature and, also, for effecting deflection of the loop formation 26 at the distal part 18 of the catheter sheath 14.

Before describing the steering control mechanism 72 in greater detail, the stylet 20 will also be described to understand the operation of the stylet 20 of the catheter 10. The stylet 20 is preferably a multi-component stylet having an outer tubular member 82, an inner tubular actuator 92, and a pull wire 100 (FIG. 9) that enable the stylet 20 to, first, deflect in a plane and, second, to adjust the shape at the distal part 24 of the stylet 20. These functions are achieved by the relative movement of one component in relation to another in a manner as described below in detail.

Figure 9:
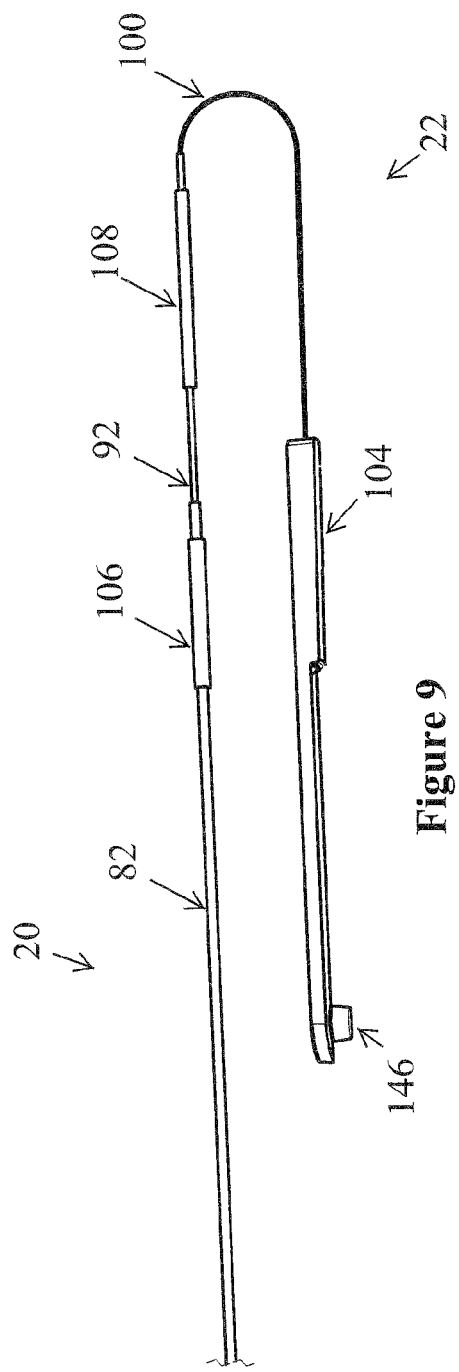
FIG. 9 shows a plan view of a proximal part of a stylet of the catheter.
Figure 11:
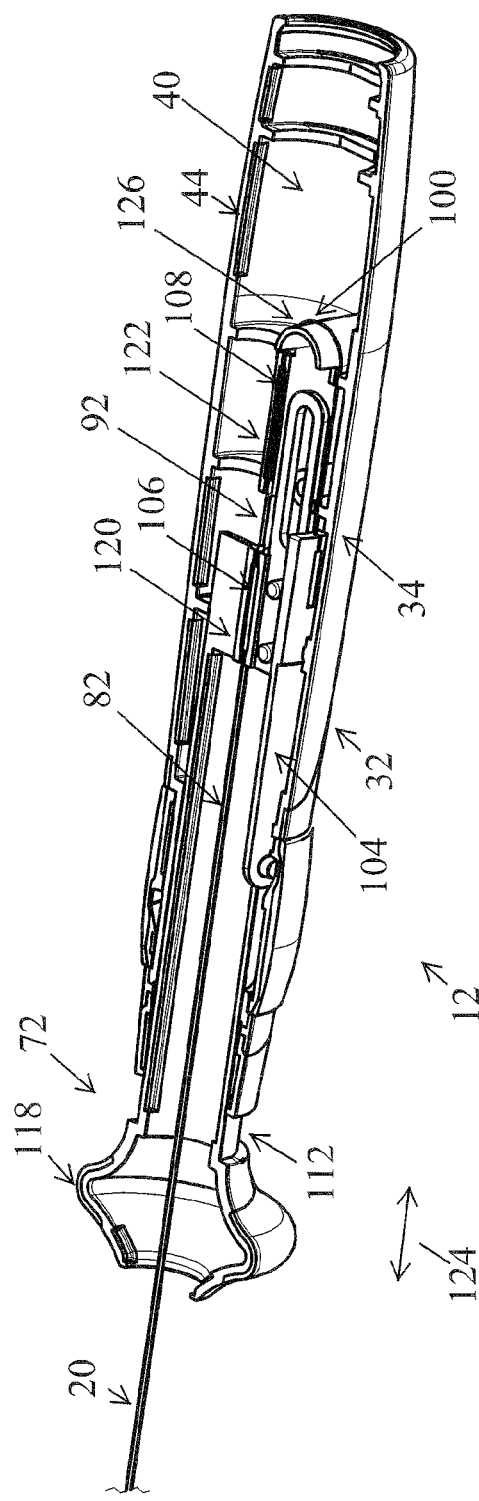
FIG. 11 shows a three-dimensional view of a part of the handle showing the interrelationship between the proximal part of the stylet and the shape adjustment mechanism.
Figure 12:
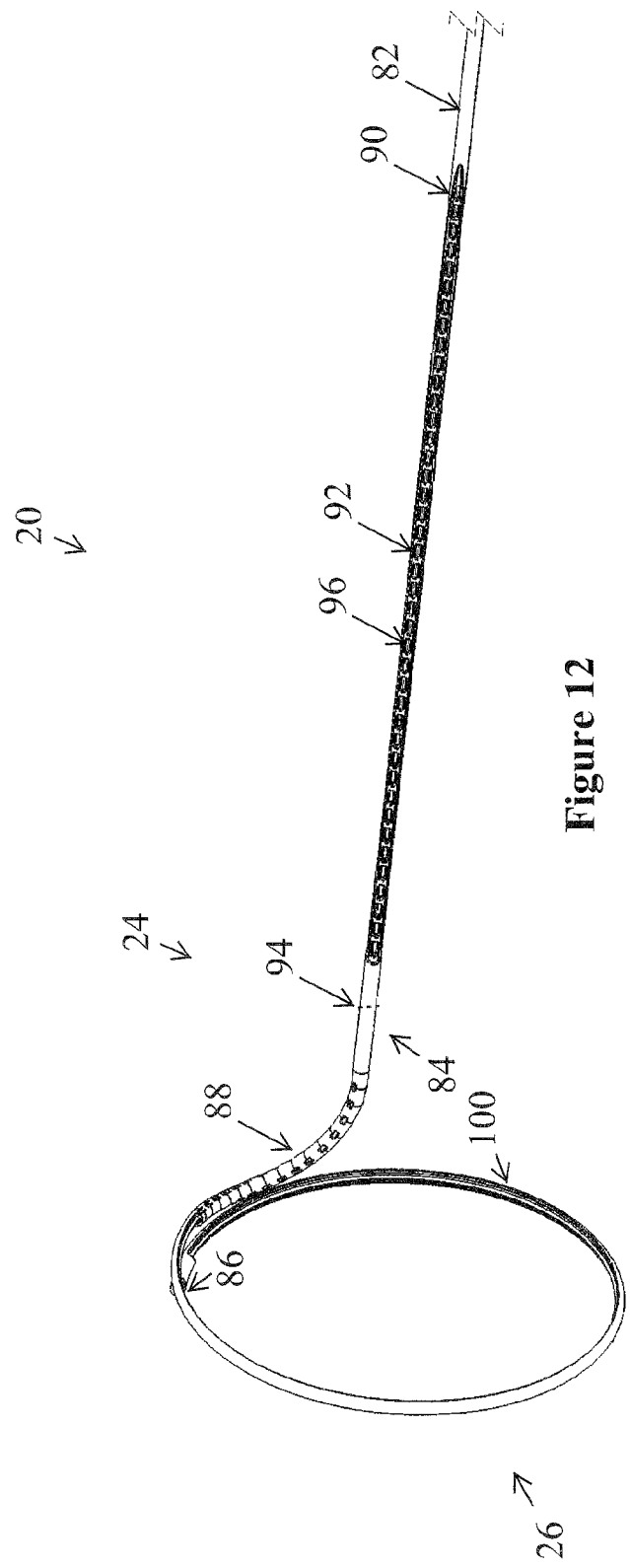
FIG. 12 shows a three-dimensional view of a distal part of the stylet.

FIG. 9 shows a proximal part 22 of the stylet 20 when it is not connected to the catheter handle 12, and FIG. 11 shows the proximal part 22 of the stylet 20 mounted in one of the shell parts 34 of the handle body 32 of the catheter handle 12. FIG. 12 shows a distal part 24 of the stylet 20 and FIG. 13 shows a distal part of a component of the stylet 20 in the form of an outer tubular member 82.

Figure 13:
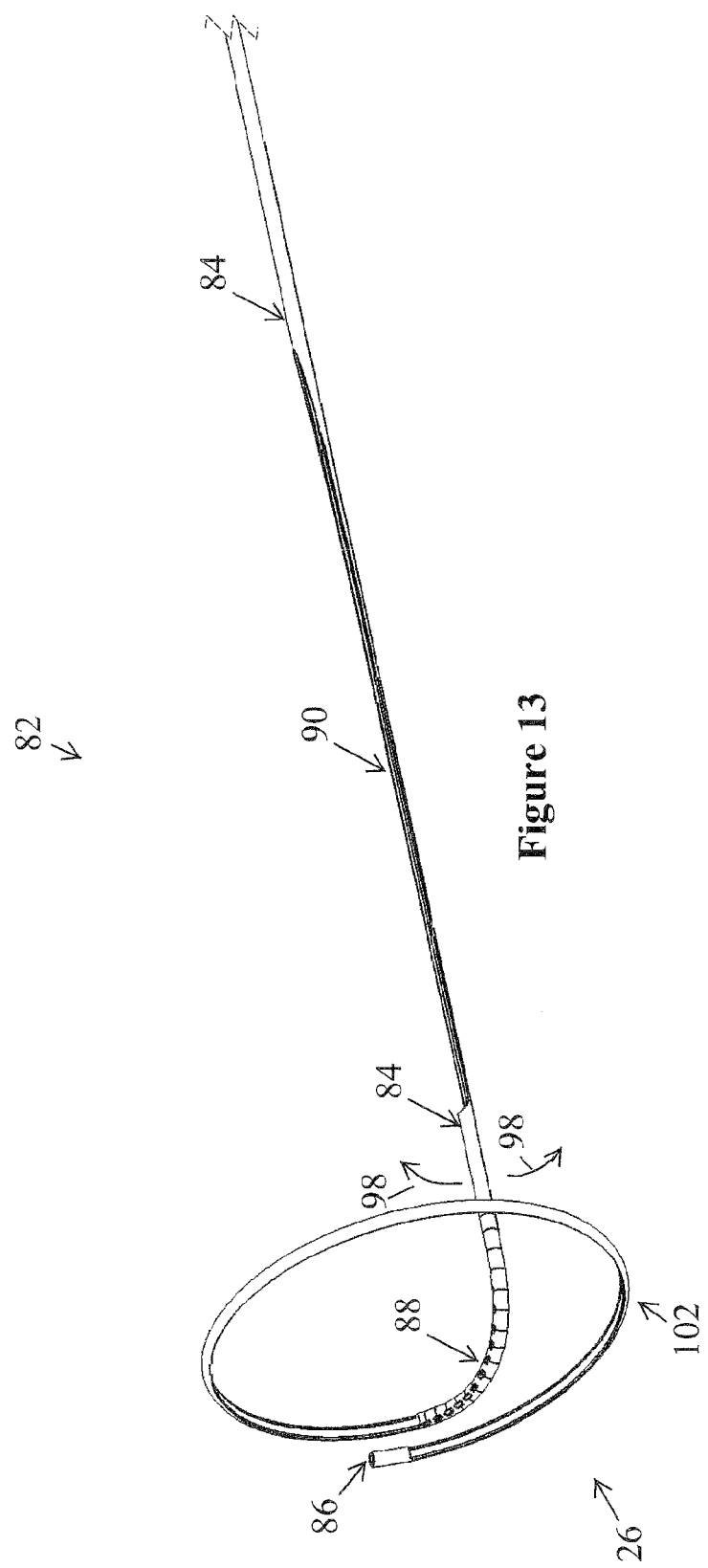
FIG. 13 shows a three-dimensional view of a distal part of an outer tube of the stylet.

The outer tubular member 82 has a distal part 84, which is shown in greater detail in FIG. 13. The distal part 84 of the outer tubular member 82 is pre-formed into the loop-shape 26 and has a distal end 86. The distal part 84 is cranked as shown at 88 so that the loop shape 26 lies in a plane transverse or perpendicular to a longitudinal axis of the outer tubular member 82. An elongate, cutaway, bend-enhancing portion 90 is formed in the distal part 84 of the tubular member 82 proximal to the cranked region 88. The portion 90 is a scalloped portion and has varying amounts cut away, increasing from a proximal end to a distal end of the cutaway portion 90 to facilitate deflection of the distal end of the loop shape 26 of the stylet 20 as will be described in greater detail below.

The stylet 20 also includes an inner, tubular actuator 92 (shown in FIG. 12). The actuator 92 has a distal end secured at 94 to the distal part 84 of the outer tubular member 82 of the stylet 20. It is to be noted that the connection point 94 is proximally arranged relative to the cranked portion 88 but distally arranged relative to the cutaway portion 90. The tubular actuator 92 has a slotted bend-enhancing region 96, which is substantially the same length and lies coincident with the cutaway portion 90 of the outer tubular member 82 of the stylet 20. Relative movement between the outer tubular member 82 and the inner tubular actuator 92 causes deflection of the loop shape 26 in the direction of arrows 98 (FIG. 13).

A shape- or size-adjusting actuator in the form of a pull wire 100 is received through lumens of the outer tubular member 82 and the tubular actuator 92 and a distal end of the pull wire 100 is fast with the distal end 86 of the outer tubular member 82. It is to be noted that there is a second longitudinally extending cutaway portion 102 formed between the distal end 86 of the outer tubular member 82 and the cranked region 88 of the outer tubular member 82 as shown in FIG. 13. This cutaway portion 102 facilitates adjustment of the size of the loop shape 26 by relative movement between the pull wire 100 and the outer tubular member 82.

As shown in FIG. 9, a proximal end of the pull wire 100 is mounted to a stylet carrier in the form of a slide 104 via a suitable mounting formation. The mounting formation includes a slot on the slide 204 (not shown) that is appropriately sized to receive the pull wire 100 or a mounting sleeve attached to the proximal end of the pull wire 100. A proximal end of the outer tubular member 82 carries a mounting sleeve 106 and, similarly, a proximal end of the tubular actuator 92 carries a mounting sleeve 108.

The steering control mechanism 72, as shown in FIG. 4, comprises an elongate, hollow cylindrical member 110 (shown in FIG. 8) that is displaceably and preferably slidably received within the passage 40 defined by the handle body 32. As in the case of other components of the catheter handle 12, the cylindrical member 110 comprises two parts 112 that, in the illustrated embodiment, are clipped together via complementary clips 114 and receiving formations 116. As in the case of the shell parts 34 of the handle body 32, the parts 112 of the cylindrical member 110 could also be hinged together and clipped or screwed closed.

A raised protuberance in the form of a radially outwardly extending knob 118 is defined at a distal end of the steering control mechanism 72 to be engaged by the thumb of a clinician for facilitating steering of the distal end of the catheter sheath 14 during use. The deflection of the distal portion 18 of the catheter sheath 12 is achieved by a push/pull motion of the control knob 118.

Referring to FIG. 11, the mounting sleeve 106 of the outer tubular member 82 of the stylet 20 is shown mounted in a seat 120 in one of the parts 112 of the steering control mechanism 72. The other part 112 could contain a corresponding part of the seat 120. The outer tubular member 82 is thus connected to the slidable cylindrical member 110 of the steering control mechanism 72. A further seat 122 is defined proximal to the seat 120 in the passage 40 of the handle body 32 and the mounting sleeve 108 of the inner tubular member 92 is made fast with the seat 122. The inner tubular member 92 is thus made fast with the handle body 32 of the catheter 10 and remains in place when the outer tubular member 82 is moved by pushing/pulling of the control knob 118. It will be appreciated that as the steering control mechanism 72 is moved in the direction of arrows 124 relative to the handle body 32, relative movement between the outer tubular member 82 of the stylet 20 and the inner tubular member 92 occurs, resulting in deflection of the distal end of the stylet 20 as shown by the arrows 98 in FIG. 13.

As illustrated in FIG. 11, the proximal part of the pull wire 100 is guided around a semispherical guidepost 126, fixedly arranged in the passage 40 of the handle body 32, and the proximal end of the pull wire 100 is preferably mounted fast with the stylet carrier 104 in the form of a slide.

In an embodiment, the catheter 10 includes a shape, or size, adjustment mechanism 128 (FIGS. 1 and 2). The shape adjustment mechanism 128 includes a shape, or size, adjuster in the foam of a collar 130 (FIGS. 1 and 2) arranged on the exterior of the handle body 32 of the catheter handle 12.

The stylet carrier 104 forms part of the shape or size adjustment mechanism 128 and is axially slidably arranged within the passage 40 of the handle body 32 of the catheter handle 12. The collar 130 is, as with other parts of the catheter handle 12, made up of two parts 132 that clip together via complementary clips 134 and receiving formations 136 (FIG. 8). In another embodiment, as illustrated in FIG. 14, the parts 132 of the collar 130 are hinged together with a wing 138 of the hinge being shown in FIG. 14. The other side of each part 132 clips together via the clips 134 and receiving formations 136.

As shown more clearly in FIG. 8, the shell parts 34 of the handle body 32 of the catheter handle 12 have a waisted region to define a recess 140 (FIG. 8). The collar 130 is received in the recess 140 and is constrained against axial motion but is free to rotate about a longitudinal axis of the handle body 32.

The recessed region 140 of each shell part 34 further has a cutaway portion 142 defined therein so that when the shell parts 34 are mated together, a longitudinally extending slot is defined in the handle body 32.

Figure 10:
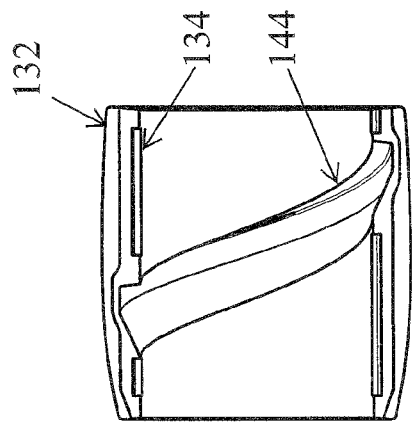
FIG. 10 shows a plan view of a part of a shape adjustment mechanism of the catheter.

The size-adjusting mechanism 128 of the catheter 10 includes complementary guide formations in the form of a camming groove 144 (shown most clearly in FIG. 10) on an internal surface of each part 132 of the collar 130. A complementary guide formation or a guide follower in the form of a pin 146 (FIG. 8) is arranged at that end of the slide 104 opposite the end to which the pull wire 100 is connected. The pin 146 protrudes through the slot in the handle body 32 formed by the cutaway portions 142 of the shell parts 34 and is received in the camming groove 144 of the collar 130. Rotation of the collar 130, therefore, translates into axial displacement of the slide 104. This axial displacement of the slide 104 results in relative movement between the pull wire 100 and the outer tubular member 82 of the stylet 20 resulting in an increase or decrease in the size of the loop shape 26 at the distal part 24 of the stylet 20 or a change in the shape of the distal part 24 of the stylet 20. Changing the shape or the size of the distal part 24 of the stylet 20 allows the physician to more accurately position the catheter 10 in the correct location. In addition, it may be helpful to change the size or the shape of the catheter tip to more easily maneuver the catheter 10 when it is in use.

Thus, by rotation of the collar 130 during use, a clinician can control the size of the loop shape 26. This is a simple, one-handed operation. It will be appreciated that the size adjustment mechanism 128 could, in addition or instead, operate as a second steering or deflection mechanism.

It is possible to adjust the effort required to displace the steering control mechanism 72 relative to the handle body 32. For this purpose, a frictional element 150 is provided. The frictional element 150 includes a screw 152 and washer assembly 154, the screw 152 being received in a threaded socket 156 in the shell part 34 of the handle body 32, as shown in FIG. 8. The screw protrudes through a slot 158 defined in a proximal extension limb 160 of one of the parts 112 of the cylindrical member 110 of the steering control mechanism 72.

Figure 6:
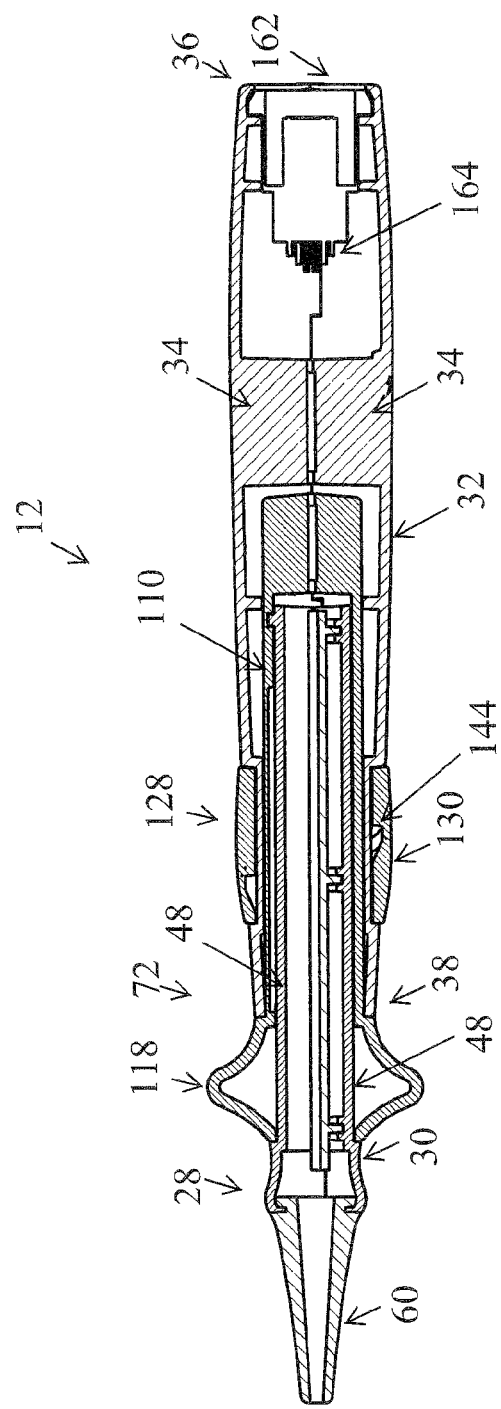
FIG. 6 shows a cross-sectional side view of a handle of the catheter with the shape release mechanism in its inoperative position.
Figure 7:
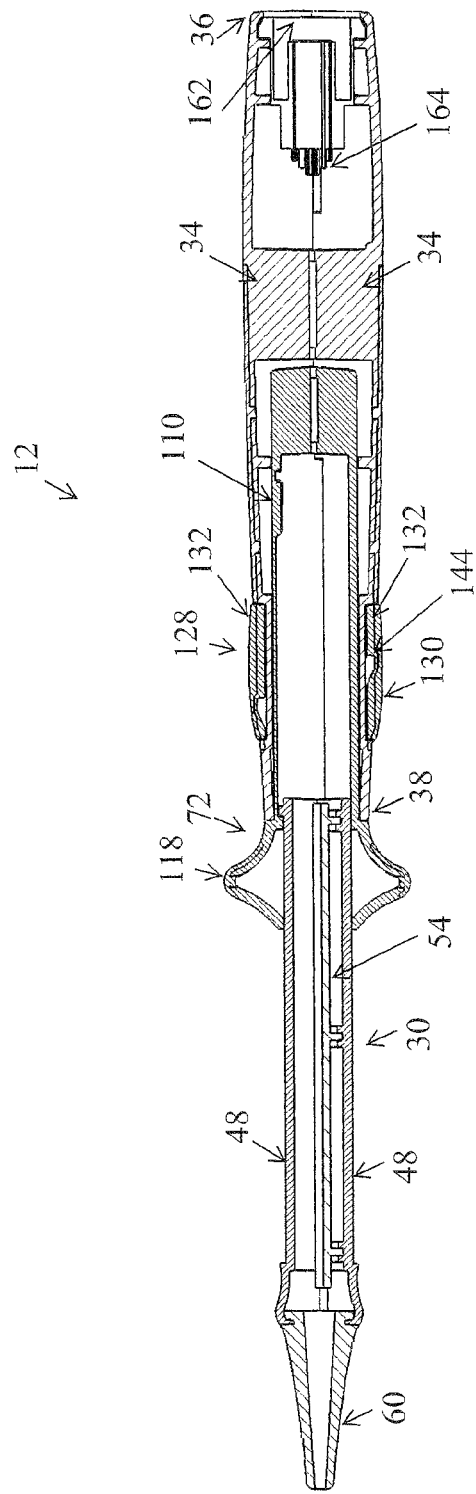
FIG. 7 shows a cross-sectional side view of a handle of the catheter with the shape release mechanism in its operative position.

The catheter 10 includes a connector 162 arranged at the proximal end 36 of the handle body 32 of the catheter handle 12. The connector 162 has terminals 164 (see also FIGS. 6 and 7) to which conductors (not shown) of the electrode 16 of the catheter sheath 14 are connected. The connector 162 sits within the handle body 32 and can be removed and replaced if necessary by separating the shell parts 34. The connector 162 connects to a patient cable of a diagnostic/therapeutic system, with which the catheter 10 is used.

It is a particular advantage of the described embodiments that a compact catheter handle is provided, which lends itself to one-handed use by a clinician. The handle 12 fits easily within the hand of the clinician and all the operating controls, such as the steering control mechanism 72 and the size adjustment mechanism 128, fall readily to hand. The steering control mechanism 72 and the size adjustment mechanism 128 are able to be manipulated one-handed by the clinician, which clinicians prefer to do. This enables them to more easily concentrate on positioning and operating the catheter 10.

In addition, catheters are becoming increasingly expensive. Due to their use in potentially biologically hazardous environments, most catheters are used once and then disposed of. Often times, this is unnecessary and the catheters can be re-processed. With the provision of a modular type of handle 12, as described above, it is an easy process to access the interior of the handle 12 to facilitate replacement or refurbishing of the various components and, more particularly, the catheter sheath 14 and the stylet 20. The handle 12 is a molding of a plastics material and is generally low cost. Thus, should the handle 12 be contaminated with bodily fluids and cannot be adequately cleaned, it is a relatively inexpensive process to dispose of the handle 12 and to replace it with a new one. Even so, because the handle 12 is made up of modular parts, if necessary, only the contaminated parts need to be replaced.

Reference throughout this specification to "one embodiment," "some embodiments" or "an embodiment" means that a particular feature, structure or characteristic described in connection with the embodiment is included in at least one embodiment of the present invention. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified, the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms "comprising," "comprised of" or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising" A and B should not be limited to devices consisting only of elements A and B. Any one of the terms "including" or "which includes" or "that includes," as used herein, is also an open term that also means including at least the elements/features that follow the term, but not excluding others. Thus, "including" is synonymous with and means "comprising."

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some, but not other, features included in other embodiments, combinations of features of different embodiments are meant to be within the scope of the invention, and form different embodiments, as would be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term "coupled," when used in the claims, should not be interpreted as being limited to direct connections only. The terms "coupled" and "connected," along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B, which may be a path including other devices or means. "Coupled" may mean that two or more elements are either in direct physical or electrical contact, or that two or more elements are not in direct contact with each other but yet still cooperate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

It will be appreciated by persons skilled in the art that numerous variations and/or modifications may be made to the disclosure as shown in the specific embodiments without departing from the scope of the claims. The present embodiments are, therefore, to be considered in all respects as illustrative and not restrictive.

The claims defining the invention are as follows:

1. A catheter shape adjustment mechanism, comprising:
   a catheter handle comprising an elongate handle body having a proximal end and a distal end with a passage extending between the proximal end and the distal end;
   a stylet carrier displaceably mounted in the passage of the elongate handle body, at least a component of a multi-component stylet mounted to the stylet carrier, wherein a distal part of the stylet has a non-rectilinear shape;
   a shape adjuster rotatably carried on an exterior of the elongate handle body, the shape adjuster being rotatable about a longitudinal axis of the elongate handle body;
   a steering control mechanism displaceably carried by the elongate handle body, the steering control mechanism configured to effect cause deflection of the multi-component stylet proximal to the distal part of the stylet having the non-rectilinear shape;
   complementary guide formations carried by the stylet carrier and the shape adjuster, wherein the stylet carrier is in the form of a slide, the slide axially slidable in the elongate handle body such that rotary motion applied to the shape adjuster imparts an axial displacement to the stylet carrier to adjust a shape of a distal part of the multi-component stylet, in use.

2. The shape adjustment mechanism of claim 1, wherein the stylet carrier includes a mounting formation for mounting a component of the multi-component stylet.

3. The shape adjustment mechanism of claim 1, wherein the catheter handle comprises a plurality of shell members that are assembled to form the elongate handle body and that can be at least partially separated from each other to access an interior of the elongate handle body.

4. The shape adjustment mechanism of claim 1, wherein the elongate handle body defines a receiving formation for rotatably receiving the shape adjuster.

5. The shape adjustment mechanism of claim 4, wherein the receiving formation is defined by a waisted region of the elongate handle body.

6. The shape adjustment mechanism of claim 5, wherein the shape adjuster is in the form of a collar received in the receiving formation of the elongate handle body.

7. The shape adjustment mechanism of claim 6, wherein the collar comprises a plurality of separable parts to enable the collar to be fitted in position about the elongate handle body.

8. The shape adjustment mechanism of claim 1, wherein the complementary guide formations comprise a camming groove defined on an operatively inner surface of the shape adjuster and a follower carried by the stylet carrier, the follower protruding through a slot defined in the elongate handle body to be received in the camming groove of the shape adjuster.

9. A catheter comprising:
a catheter handle comprising an elongate handle body having a proximal end and a distal end and a passage extending between the proximal end and the distal end;
a shape adjustment mechanism carried by the elongate handle body, the shape adjustment mechanism comprising:
  a stylet carrier displaceably mounted in the passage of the elongate handle body;
  a shape adjuster rotatably carried on an exterior of the elongate handle body, the shape adjuster being in the form of a slide axially displaceable in the elongate handle body and being rotatable about a longitudinal axis of the elongate handle body, the stylet carrier and the shape adjuster having complementary guide formations so that rotary motion applied to the shape adjuster imparts an axial displacement to the stylet carrier; and
a multi-component stylet carried by the catheter handle with a distal part of the multi-component stylet being formed into a non-rectilinear shape, the multi-component stylet comprising at least a pull wire connected to the stylet carrier and a tubular member arranged in the elongate handle body so that relative movement between the stylet carrier, under the action of the shape adjuster, and the elongate handle body results in a change of shape of the distal part of the multi-component stylet; and
a steering control mechanism displaceably carried by the elongate handle body, the steering control mechanism configured to cause deflection of the multi-component stylet proximal to the distal part of the multi-component stylet having the non-rectilinear shape.

10. The catheter of claim 9, wherein the pull wire is mounted to the stylet carrier, one of the tubular member and another tubular member being mounted to the steering control mechanism, and the other of the tubular member and the another tubular member being fast with the elongate handle body.

11. The catheter of claim 9, further comprising a catheter sheath mounted to a distal end of the catheter handle, the catheter sheath defining a lumen in which the multi-component stylet is received so that the predetermined shape at the distal part of the multi-component stylet is imparted to a distal part of the catheter sheath.

12. The catheter of claim 11, wherein the catheter sheath is carried on a shape release mechanism, the shape release mechanism being displaceably carried by the elongate handle body.

13. The catheter of claim 9, wherein the stylet carrier is axially slidable in the elongate handle body.

14. The catheter of claim 9, wherein the stylet carrier includes a mounting formation for mounting a component of the multi-component stylet.

15. The catheter of claim 9, wherein the elongate handle body defines a receiving formation for rotatably receiving the shape adjuster.

16. The catheter of claim 15, wherein the receiving formation is defined by a waisted region of the elongate handle body.

17. The catheter of claim 16, wherein the shape adjuster is in the form of a collar received in the receiving formation of the elongate handle body.

18. The catheter of claim 9, wherein the complementary guide formations comprise a camming groove defined on an operatively inner surface of the shape adjuster and a follower carried by the stylet carrier, the follower protruding through a slot defined in the elongate handle body to be received in the camming groove of the shape adjuster.

19. A catheter comprising:
a catheter handle comprising an elongate handle body having a proximal end and a distal end and a passage extending between the proximal end and the distal end;
a shape adjustment mechanism carried by the elongate handle body, the shape adjustment mechanism comprising:
  a stylet carrier displaceably mounted in the passage of the elongate handle body;
  a shape adjuster rotatably carried on an exterior of the elongate handle body, the shape adjuster being in the form of a slide axially displaceable in the elongate handle body and being rotatable about a longitudinal axis of the elongate handle body, the stylet carrier and the shape adjuster having complementary guide formations so that rotary motion applied to the shape adjuster imparts an axial displacement to the stylet carrier; and
a multi-component stylet carried by the catheter handle with a distal part of the multi-component stylet being formed into a non-rectilinear shape, the multi-component stylet comprising:
  at least a pull wire mounted to the stylet carrier; and
  a tubular member arranged in the elongate handle body so that relative movement between the stylet carrier, under the action of the shape adjuster, and the elongate handle body results in a change of shape of the distal part of the multi-component stylet; and
a steering control mechanism displaceably carried by the elongate handle body, the steering control mechanism configured to effect deflection of the multi-component stylet proximal to the distal part of the multi-component stylet having the non-rectilinear shape, wherein one of the tubular member and another tubular member being mounted to the steering control mechanism and the other of the tubular member and the another tubular member being fast with the elongate handle body.

* * * * *